US009909084B2

(12) United States Patent
Mercier et al.

(10) Patent No.: US 9,909,084 B2
(45) Date of Patent: Mar. 6, 2018

(54) LIQUID/LIQUID EXTRACTION WITH A SOLVENT COMPRISING AT LEAST 5 CARBON ATOMS AND 1 OR 2 OXYGEN ATOMS

(75) Inventors: Eglantine Mercier, Rambouillet (FR); Jacques Legrand, Neuily sur Eure (FR); Alex Saunois, Nogent-le-Roi (FR)

(73) Assignee: Laboratoires Expanscience, Courbevoie (FR)

( * ) Notice: Subject to any disclaimer, the term of this patent is extended or adjusted under 35 U.S.C. 154(b) by 460 days.

(21) Appl. No.: 14/235,293

(22) PCT Filed: Jul. 30, 2012

(86) PCT No.: PCT/FR2012/000320
§ 371 (c)(1),
(2), (4) Date: Jan. 27, 2014

(87) PCT Pub. No.: WO2013/014344
PCT Pub. Date: Jan. 31, 2013

(65) Prior Publication Data
US 2014/0363559 A1 Dec. 11, 2014

(30) Foreign Application Priority Data
Jul. 28, 2011 (FR) .................................. 11 56936

(51) Int. Cl.
*C07C 29/86* (2006.01)
*C11B 13/00* (2006.01)
*A61Q 19/00* (2006.01)
*A61Q 19/08* (2006.01)
*A61Q 19/06* (2006.01)
*A61K 8/97* (2017.01)
*A61K 8/99* (2017.01)
*C11B 1/04* (2006.01)
*C11B 1/10* (2006.01)
*A23L 33/105* (2016.01)
*A23L 33/11* (2016.01)
*A23L 33/15* (2016.01)

(52) U.S. Cl.
CPC ............ *C11B 13/00* (2013.01); *A23L 33/105* (2016.08); *A23L 33/11* (2016.08); *A23L 33/15* (2016.08); *A61K 8/97* (2013.01); *A61K 8/99* (2013.01); *A61Q 19/00* (2013.01); *A61Q 19/06* (2013.01); *A61Q 19/08* (2013.01); *C11B 1/04* (2013.01); *C11B 1/10* (2013.01)

(58) Field of Classification Search
CPC .................................................... A23D 7/00
See application file for complete search history.

(56) References Cited

U.S. PATENT DOCUMENTS

| 2,530,809 | A | | 11/1950 | Christenson et al. | |
|---|---|---|---|---|---|
| 2,610,195 | A | * | 9/1952 | Gebhart | 552/545 |
| 2,648,687 | A | * | 8/1953 | Van Ness | 552/545 |
| 2,772,297 | A | * | 11/1956 | Laquer | 552/545 |
| 2,794,035 | A | * | 5/1957 | Hummel | 552/545 |
| 2,843,610 | A | * | 7/1958 | Brown et al. | 552/545 |
| 2,866,781 | A | * | 12/1958 | Bowers et al. | 530/208 |
| 3,332,969 | A | * | 7/1967 | Hutt, Jr. | 552/545 |
| 3,804,819 | A | | 4/1974 | Wengrow et al. | |
| 3,983,147 | A | * | 9/1976 | Senda et al. | 554/189 |
| 4,057,541 | A | * | 11/1977 | Weber et al. | 540/16 |
| 4,425,275 | A | * | 1/1984 | Crawford et al. | 552/544 |
| 2006/0166951 | A1 | * | 7/2006 | Sanbom | 514/169 |
| 2012/0209018 | A1 | | 8/2012 | Piccirilli | |

FOREIGN PATENT DOCUMENTS

CN 101318988 A 12/2008
EP 1 733 731 A1 12/2006
(Continued)

OTHER PUBLICATIONS

Gao et al., "Extraction of sterol from raw glycerol comprises adding alkaline ethanol aqueous solution into extracted glycerol, heating and saponifying, adding extraction agent, stirring, leaving or centrifuging, washing, extracting, and drying," Database WPI Week 200915, Thomas Scientific, London, GB, AN 2009-B34086, XP002669763 (2009).
International Search Report for International Application No. PCT/FR2012/000320 dated May 27, 2013.
"Substances classified as carcinogenic, mutagenic and toxic for reproduction (CMR) and other substances of concern in consumer products", Environmental Research of the Federal Ministry of the Environment, Nature Conservation and Nuclear Safety, Project No. (FKZ) 3707 61 300, Report No. (UBA-FB) 001434 (Apr. 2011).

*Primary Examiner* — D. Lawrence Tarazano
*Assistant Examiner* — Philip A Dubois
(74) *Attorney, Agent, or Firm* — Foley & Lardner LLP

(57) ABSTRACT

The present invention relates to an extraction process of an unsaponifiable fraction contained in an oil or a vegetable butter, in an oil originating from a micro-organism, in a concentrate of oil or butter or of oil originating from a micro-organism, or in a co-product of the refining industry for vegetable oils, such as deodorization exhaust and distillates of physical refining, or oils originating from micro-organisms, comprising at least:
A) a transformation step of said oils, of said butter or said co-product of the refining industry for vegetable oils or oils originating from micro-organisms in hydro-alcoholic solution, especially via a saponification step, and
B) an extraction step of the hydro-alcoholic solution in which the fatty fraction is separated from unsaponifiable fraction by liquid/liquid extraction,
said process being characterized in that at least the liquid/liquid extraction step of the step B is performed by using a first solvent system comprising a solvent content selected from the solvents comprising at least 5 carbon atoms and one or two oxygen atoms in the form of either ether function, or ketone function, or ester function, of at least 50% in volume relative to the total volume of the first solvent system, as well as fractions obtained by said process.

23 Claims, No Drawings

(56) References Cited

FOREIGN PATENT DOCUMENTS

| | | |
|---|---|---|
| FR | 2678632 A1 | 1/1993 |
| FR | 2762512 A1 | 10/1998 |
| FR | 2951736 A1 | 4/2011 |
| WO | WO-2011/048339 A1 | 4/2011 |

* cited by examiner

LIQUID/LIQUID EXTRACTION WITH A SOLVENT COMPRISING AT LEAST 5 CARBON ATOMS AND 1 OR 2 OXYGEN ATOMS

The present invention relates to an extraction process of unsaponifiable fractions, especially partial or total, from oils or vegetable butters or from oils originating from microorganisms.

Unsaponifiables or unsaponifiable fractions of a fatty body are constituted by compounds which, after prolonged action of an alkaline base, remain insoluble in water and can be extracted by an organic solvent.

The majority of unsaponifiables of oils or vegetable butters comprises several large families of substances. Examples of these large families are saturated or unsaturated hydrocarbons, aliphatic or terpenic alcohols, sterols, tocopherols, carotenoid pigments, xanthophiles, as well as specific families, especially one or two, for some of the oils and butters.

Usual processes for obtaining unsaponifiables from vegetable oils and vegetable butters aim at extracting all or part of the large families they are composed of, allowing to prepare the partial or total fractions of unsaponifiables.

The unsaponifiable partial or total fractions are especially preferred for their pharmacological, cosmetic and nutritional properties.

The usual processes for obtaining unsaponifiables from vegetable oils and vegetable butters comprise a saponification step of the fatty matter and an extraction of the target product (unsaponifiable) by an organic solvent.

The most commonly used solvents are solvents of oils, such as alkanes (hexane, heptane, . . . ) and chlorinated solvents (1,2-dichloroethane or DCE, trichloroethane, 1-chlorobutane, carbon tetrachloride, . . . ). Of these, DCE and 1-chlorobutane are the best candidates, especially with respect to their extraction yield and their selectivity.

However, on an industrial scale, the toxicity of the solvent used, as well as its chemical stability, must be taken into account.

Chlorinated solvents frequently exhibit unwanted toxicity, ecotoxicity and/or hazard.

On this basis, chlorinated solvents, and in particular 1,2-dichloroethane (DCE) and 1-chlorobutane, present three major disadvantages: they can be degraded in basic medium (which is the case for soapy saponification solutions), they are classified among toxic solvents, especially CMR for DCE, and they cause a negative impact on the environment (ecotoxicity).

Also, as much from an economic point of view as from an environmental point of view, processes for obtaining unsaponifiable fractions can require the use of quantities of organic solvents not adapted for the viability of the process, have an unsatisfactory number of extraction steps, be too slow and/or present unsatisfactory phase separations, for example by causing an unwanted emulsion.

The aim of the present invention is therefore to resolve in full or part the problems mentioned hereinabove. In particular, the aim of the invention is to provide a process having a higher overall yield, an improved extraction rate in one or more unsaponifiable fractions, more economical, more direct, friendlier for the environment, requiring a lower quantity of organic solvent, easier to execute, faster, generating less toxic and/or less dangerous conditions, improving the separation of phases, producing an unsaponifiable with a yield, cost and/or selectivity at least comparable to existing processes.

In particular, it is preferable that the solvent(s) involved is/are less dangerous, less toxic, especially non-CMR-classified, is/are chemically more stable than 1,2-dichloroethane and/or 1-chlorobutane and/or extract unsaponifiable with a yield and/or selectivity at least comparable to the yields and selectivities obtained by using 1,2-dichloroethane and/or 1-chlorobutane.

Those solvents called <<CMR-classified>> can be those presented in the list in appendix of the directive 2009/2/CE of Jan. 15, 2009, this first list being called <<list CMR UE1>> hereinbelow, those listed in the European Regulatory Classification for carcinogenic, mutagenic and toxic chemical products for reproduction—31st ATP, 2009, this second list being called <<list CMR UE2>> hereinbelow, and/or those listed in the list <<Chemicals known or suspected to cause cancer or reproductive toxicity>> of Sep. 1 2009 set up by the <<California department of public health, occupational health branch, California safe cosmetic program>> associated with the <<California Safe Cosmetics Act of 2005>>, this third list being called <<list CMR US>> hereinbelow.

When the expression list CMR UE is used in the present text, this means list CMR UE1 and/or CMR UE2.

The solvents used in the present invention are therefore free of the following solvent families and solvents:
   some alkanes, such as hexane, heptane,
   some aromatic hydrocarbons such as naphthalene,
   some halogenated solvents, in particular the chlorinated solvents (1,2-dichloroethane or DCE, trichloroethane, dichloromethane, trichloromethane (chloroform), dichloroethylene, carbon tetrachloride, . . . ), or 1-chorobutane.

One of the more particular aims is to obtain a specific unsaponifiable fraction, for example having a higher content in some compounds, or fractions, and optionally a less high in others, in particular comprising only one or some of the families of compounds of the total unsaponifiable.

The unsaponifiables can be composed of numerous constituents, in particular comprising the large families of substances defined hereinabove and/or specific families. It may be preferred to extract as completely as possible at least one of these families, especially at least two, in particular at least three, quite particularly at least four, or even at least five, quite particularly at least six, and even more particularly all the families making up unsaponifiable of a given oil or butter.

The aim of the process according to the invention can quite particularly be to improve the overall yield of unsaponifiable and/or the extraction rate of one or more fractions, especially two, three or four fractions.

In other words, the aim of the process according to the invention can be either to produce a specific partial fraction of unsaponifiable, especially having a content enriched in at least one of the families comprising unsaponifiable, or even specifically extracting one or more particular compounds of unsaponifiable, or to produce the total unsaponifiable fraction.

The aim of the present invention is therefore an extraction process of an unsaponifiable fraction, especially partial or total, contained in an oil or a vegetable butter, in an oil originating from a micro-organism, in a concentrate of oil or vegetable butter or oil originating from a micro-organism, or in a co-product of the refining industry for vegetable oils, such as deodorisation exhaust and distillates of physical refining, or oils originating from micro-organisms, comprising at least:

A) a transformation step of said oils, said butter or said co-product of the refining industry for vegetable oils, such as deodorisation exhaust and distillates of physical refining, or oils originating from micro-organisms into a hydro-alcoholic solution, especially via a saponification step B) an extraction step of the hydro-alcoholic solution in which the fatty fraction is separated from unsaponifiable fraction by liquid/liquid extraction, and C) optionally, a purification step of the unsaponifiable, said process being characterised in that at least the liquid/liquid extraction step of step B is performed by using a first solvent system comprising a content in solvent selected from the solvents comprising at least 5 carbon atoms, advantageously between 5 and 9 carbon atoms, in particular from 5 to 8 carbon atoms, and one or two oxygen atoms, in the form of either ether function, or ketone function, or ester function, of at least 50% in volume relative to the total volume of the first solvent system.

In the sense of the present invention <<solvent system>> means a single solvent or a mixture of solvents.

By <<microorganism>> is meant any living microscopic organism such as bacteria or fungi, in particular yeasts and moulds.

Advantageously, the saponification step is conducted in the presence of excess base such potash so as to ensure full conversion of the triglycerides into soaps.

The liquid/liquid extraction step typically comprises a continuous phase and a dispersed phase.

By <<continuous phase>> is meant the (organic or aqueous) phase filling the extraction column; by <<dispersed phase>> is meant the (organic or aqueous) phase which is present in the form of droplets in the extraction column.

The Applicant has surprisingly found that several technical characteristics, advantageously combined together, allow the optimizing of liquid/liquid extraction and in particular the action on the yield and on the selectivity of extraction (obtaining an unsaponifiable enriched with a given fraction).

This particularly relates to:
adjustment of the alcohol content of the hydro-alcoholic solution obtained after step A;
the type of continuous phase during extraction step B;
the ratio between the flow rates of the hydro-alcoholic solution (or aqueous phase) and the solvent (or organic phase), or the ratio between the volumes of contacted hydro-alcoholic solution and solvent;
the type of unsaponifiable under consideration.

In a particular embodiment, the process according to the present invention comprises a purification step C, following extraction step B, said purification step C being advantageously selected in the group consisting in crystallisations, distillations, rectifications, precipitations, filtrations, especially nano- and ultrafiltrations, deodorisations, liquid chromatographies and liquid/liquid extractions.

The purification step C is typically performed by using the first solvent system such as defined hereinabove, comprising a content in solvent selected from solvents comprising at least 5 carbon atoms, advantageously between 5 and 9 carbon atoms, in particular between 5 and 8 carbon atoms, and one or two oxygen atoms, in the form of either ether function, or ketone function, or ester function, of at least 50% in volume relative to the total volume of the first solvent system.

In particularly advantageous manner, the process of the invention comprises a step A' to adjust the alcohol content of the hydro-alcoholic solution obtained after step A, in particular with a view to optimizing the following extraction step B.

In one particular embodiment, a water/alcohol mixture is added to the hydro-alcoholic solution, this mixture possibly comprising 0 to 40% alcohol, more particularly 0 to 20% alcohol and typically between 0 and 16% alcohol.

The alcohol used can be chosen from among ethanol, propanol, n-butanol or isopropanol.

The weight of the added water/alcohol mixture to adjust the alcohol content is 1 to 5 times the weight of hydro-alcoholic solution obtained after saponification, more particularly from 1 to 4 times the weight of hydro-alcoholic solution obtained after saponification, and typically from 1 to 2 times the weight of hydro-alcoholic solution obtained after saponification.

When the first solvent system comprises a content in solvent or in a mixture of solvents selected in a list of X %, this signifies that the complementary percentage corresponds to one or more organic solvents, not featured in this list.

According to a particular embodiment, the first solvent system is devoid of tertbutyl ethers, in particular of ETBE and/or MTBE, or devoid of terpenes in particular of limonene and alpha-pinene.

In particular, said solvent comprising at least 5 carbon atoms and one or two oxygen atoms is selected from methylketones, especially methyl isobutyl ketone or MIBK and 2-heptanone, propionates, especially ethyl propionate, n-butyl propionate and isoamyl propionate, propylethers, especially diisopropyl ether or DIPE, and their mixtures.

The CAS numbers of these different solvents are the following, methyl isobutyl ketone or MIBK: 108-10-1; 2-heptanone: 110-43-0; ethyl propionate: 105-37-3; butyl propionate: 590-01-2; isoamyl propionate: 105-68-0; diisopropyl ether or DIPE: 108-20-3.

In particularly advantageous manner, the extraction solvent is chosen from among methylketones in particular methyl isobutyl ketone or MIBK and 2-heptanone, propionates in particular ethyl propionate, n-butyl propionate and isoamyl propionate, and mixtures thereof.

According to a particular characteristic of the present invention, said solvent is a methylketone, such as methyl isobutyl ketone or MIBK.

According to another particular characteristic of the present invention, said solvent is 2-heptanone.

According to another particular characteristic of the present invention, the said solvent is at least one propionate, in particular ethyl propionate, n-butyl propionate and isoamyl propionate.

According to another particular characteristic of the present invention, DIPE is used in a mixture with another extraction solvent chosen from among methylketones in particular methyl isobutyl ketone or MIBK and 2-heptanone, propionates in particular ethyl propionate, n-butyl propionate and isoamyl propionate.

In particularly advantageous manner, the liquid/liquid extraction solvents of the invention contain between 5 and 8 carbon atoms and therefore have small carbon chains and hence the advantage of being sufficiently lipophilic in particular to extract the unsaponifiables from the oils and subsequently to be easily separated from the unsaponifiables after the extraction thereof.

In the sense of the present invention <<total fraction>> means a fraction that comprises all of the families of substances composing the unsaponifiable present in the vegetable oil or in vegetable butter or in oil originating from a micro-organism in question.

In the sense of the present invention <<partial fraction>> means a fraction that comprises at least one of the families of substances composing the unsaponifiable present in the oil or vegetable butter or oil originating from a micro-organism in question.

Quite particularly advantageously, the invention relates to a process in which step B) comprises, or consists in, liquid/liquid extraction with the first solvent system.

According to a particular embodiment, the invention relates to a process in which step C) comprises, or consists in, crystallisation, precipitation or liquid chromatography with the first solvent system.

According to an even more particular embodiment, the process comprises a step B) comprising, or consisting in, liquid/liquid extraction with a first solvent system and a step C) comprising, or consisting in crystallisation, precipitation or liquid chromatography with a first solvent system identical or different to that used in step B).

Quite particularly, step C) can allow purification of the unsaponifiable fraction, enrich it in one or more families of substances that compose the unsaponifiable present in the vegetable oil, oil originating from a micro-organism or vegetable butter in question.

In particular, this can allow for separation of a specific fraction of soy unsaponifiable, such as sterolic compounds, tocopherols and/or squalene or avocado unsaponifiable, such as furanic, trihydroxylated and/or sterolic compounds.

The process according to the invention, especially in its steps A), B) and C), can be devoid of a complexing step involving the first solvent system.

The first solvent system can comprise a content in solvent selected from solvents comprising at least 5 carbon atoms, or even 5 to 8, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, and their mixtures, of at least 60%, especially at least 75%, in particular at least 90%, more particularly at least 95%, even more particularly at least 99% in volume, relative to the total volume of the first solvent system.

In particular, the first solvent system consist in solvent(s) comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, or a mixture thereof.

The first solvent system can comprise a content of a single solvent selected from solvents comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, of at least 60%, especially at least 75%, in particular at least 90%, more particularly at least 95%, even more particularly at least 99% in volume relative to the total volume of the first solvent system.

According to a variant, the first solvent system consist in a solvent comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate.

According to a particular embodiment, the first solvent system has a density inferior to 1, and especially inferior or equal to 0.9.

More particularly, the first solvent system has a density spread with the dilute hydro-alcoholic solution (DHS) superior to 0.1 and more particularly superior to 0.13, and specifically superior to 0.2.

Advantageously according to the present invention, the first solvent system further comprises hexamethyldisiloxane (HMDS), typically at a content of between 0.1 and 49% in volume, relative to the total volume of the first solvent system.

The CAS numbers HMDS is 107-46-0.

Advantageously, the liquid/liquid extraction step B, as well as optionally the purification step C, is (are) performed by using a first solvent system comprising HMDS especially.

According to a particular embodiment, the first solvent system can comprise:
  a content in solvent selected from the solvents comprising at least 5 carbon atoms, in particular from 5 to 8 carbon atoms, and one or two oxygen atoms in the form of either ether function, or ketone function, or ester function, in particular selected from methylketones, especially MIBK, 2-heptanone, propionates, especially ethyl propionate, n-butyl propionate, isoamyl propionate, propylethers, especially DIPE, and their mixtures, of at least 50% in volume relative to the total volume of the first solvent system, and
  HMDS, especially in a content ranging from 0.1 to 49%, quite particularly from 0.5 to 30%, or even from 1 to 20%, and quite particularly from 5 to 10% in volume, relative to the total volume of the first solvent system.

The first solvent system can comprise:
  a content in solvent selected from solvents comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, and their mixtures, of at least 60%, especially at least 75%, in particular at least 90%, and more particularly at least 95% in volume relative to the total volume of the first solvent system, and
  HMDS, especially in a content ranging from 0.1 to 40%, quite particularly from 0.5 to 25%, or even from 1 to 10%, and quite particularly from 5 to 10% in volume relative to the total volume of the first solvent system.

In particular, the first solvent system is constituted by:
  solvent comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, or a mixture of the latter, advantageously at a content of at least 50% in volume, relative to the total volume of the first solvent system, and
  HMDS, especially in a content ranging from 0.1 to 49%, quite particularly from 0.5 to 30%, or even from 1 to 20%, and quite particularly from 5 to 10% in volume relative to the total volume of the first solvent system.

The first solvent system can comprise:
  a content in solvent selected from solvents comprising at least 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, of at least 60%, especially at least 75%, in particular at least 90%, more particularly at least 95%, even more particularly at least 99% in volume relative to the total volume of the first solvent system, and HMDS, especially in a content ranging from 0.1 to 40%, quite particularly from 0.5 to 25%, or even from 1 to 10%, and quite particularly from 5 to 10% in volume relative to the total volume of the first solvent system.

According to a variant, the first solvent system is constituted by:

a solvent comprising at least, 5 carbon atoms, or even from 5 to 8 carbon atoms, and one or two oxygen atoms in the form of ether, ketone or ester function, in particular selected from methylketones, especially MIBK, 2-heptanone, propionates, especially ethyl propionate, n-butyl propionate, isoamyl propionate, propylethers, especially DIPE, advantageously at a content of at least 50% in volume, relative to the total volume of the first solvent system, and HMDS, especially in a content ranging from 0.1 to 49%, quite particularly from 0.5 to 25%, or even from 1 to 10%, and quite particularly from 5 to 10% in volume relative to the total volume of the first solvent system.

According to a particular embodiment, the first solvent system comprises a content of CMR solvent(s), in particular present on the list CMR UE1, UE2, and/or US, inferior or equal to 10%, especially inferior or equal to 5%, in particular inferior or equal to 2%, quite particularly inferior or equal to 1%, even more particularly inferior or equal to 0.5%, or even leinferior or equal to 0.1% in volume, relative to the total volume of the first solvent system.

Even more particularly, the first solvent system is devoid of solvents present on the list CMR UE1, UE2 and/or US.

The solvents used in the first solvent system exhibit a purity of at least 90%, especially of at least 95%, in particular of at least 98%, quite particularly of at least 99%, or even of at least 99.5%.

In particular, the step A) of transformation of oil, butter or co-product of the refining industry for vegetable oils or micro-organisms into a hydro-alcoholic solution, especially via a saponification step, is performed in a second solvent system comprising a content in solvent selected from C2 to C4 alcohols, and especially ethanol, n-propanol, iso-propanol, butanol, in particular n-butanol, MeTHF and their mixtures of at least 50% in volume, relative to the total volume of the second solvent system.

The second solvent system can comprise a content in solvent selected from C2 to C4 alcohols, and especially ethanol, n-propanol, iso-propanol, butanol, in particular n-butanol, MeTHF and their mixtures of at least 60%, especially at least 75%, in particular at least 90%, more particularly at least 95%, even more particularly at least 99% in volume, relative to the total volume of the second solvent system.

In particular, the second solvent system is constituted by ethanol, n-propanol, iso-propanol, butanol, MeTHF or a mixture thereof.

The second solvent system can comprise a content in solvent selected from C2 to C4 alcohols, and especially ethanol, n-propanol, iso-propanol, butanol, in particular n-butanol, and MeTHF, of at least 50%, especially at least 75%, in particular at least 90%, more particularly at least 95%, even more particularly at least 99% in volume relative to the total volume of the second solvent system.

According to a particular embodiment, the second solvent system comprises a content of solvent(s) present on the list CMR UE1, UE2 and/or US, less than or equal to 10%, especially inferior or equal to 5%, in particular inferior or equal to 2%, quite particularly inferior or equal to 1%, even more particularly inferior or equal to 0.5%, or even inferior or equal to 0.1% in volume relative to the total volume of the second solvent system.

Even more particularly the second solvent system is devoid of solvents present on the list CMR UE1, UE2 and/or US.

The solvents used in the second solvent system exhibit a purity of at least 90%, especially of at least 95%, in particular of at least 98%, quite particularly of at least 99%, or even of at least 99.5%.

In the sense of the present invention <<diluted hydroalcoholic solution (DHS)>> means the saponification reaction medium diluted in advantageously demineralized water and comprising especially water and one or more highly polar solvents, in particular selected from alcohols, for example C2 to C4 alcohols, and MeTHF.

The diluted hydroalcoholic solution (DHS) can comprise a water content superior or equal to 50%, especially superior or equal to 60%, in particular superior or equal to 65%, quite particularly superior or equal to 70%, or even superior or equal to 72% in volume relative to the volume of the hydroalcoholic solution.

The diluted hydroalcoholic solution (DHS) can comprise a water content inferior or equal to 95%, especially inferior or equal to 90%, in particular inferior or equal to 85%, quite particularly inferior or equal to 80%, or even inferior or equal to 75% in volume relative to the volume of the hydroalcoholic solution.

Quite particularly, the DHS can comprise a titre of alcohol of between 10 and 50%, more particularly between 11 and 40%, and typically between 12 and 28%, by weight, the titre of alcohol being a function of the solvent under consideration and of the type of unsaponifiable.

More particularly, during the extraction of unsaponifiable from avocado, the DHS may have an alcohol titre of between 10 and 20%, typically between 10 and 15%.

During the extraction of unsaponifiable from soybean, the DHS may have an alcohol tire of between 20 and 30% and typically between 22% and 28%.

The titre of alcohol is adjusted to optimise extraction, especially in terms of phase separation between the DHS and the first solvent system. The adjustment of the titre of alcohol, advantageously coupled with adjustment of the ratio between the volumes or flow rates of DHS and solvent placed in contact and with the type of continuous phase, allow improved efficacy, selectivity and/or quality of the extraction operation B. The effect of optimising this parameter is to improve the productivity of the process in particular by maximising the extraction yield at step B, by decreasing the quantity of solvent to be used, by reducing the contact time between the phases, by reducing energy consumption, facilitating dephasing and/or by decreasing the risk of emulsions, and by decreasing the amount of waste generated. It also allows improved selectivity of the extraction operation by favouring extraction of one, two, three, four, or even of all the fractions of unsaponifiable and/or the quality of the extraction by limiting the extraction of related compounds, especially by optimising the separation of phases and limiting the amount of water used in the organic phase.

Another object of the present invention is an extraction process of an unsaponifiable fraction, especially partial or total, contained in a vegetable oil, an oil originating from a micro-organism, a vegetable butter or a co-product of the refining industry for vegetable oils, especially avocado and/or soy, or oils originating from micro-organisms comprising at least:
- A) a saponification step by which said oil, said butter or said co-product of the refining industry for vegetable oils or oils originating from micro-organisms is transformed after saponification into a hydro-alcoholic solution,
- B) an extraction step of the hydro-alcoholic solution by a first solvent system such as defined hereinabove.

More particularly, the extraction process of unsaponifiable fraction according to the present invention is such that liquid/liquid extraction is performed by putting the DHS in contact with a first solvent system, especially in a counter-current process, in which the ratio (volume/volume) of solvent system/DHS ranges from 0.1 to 10, advantageously from 0.1 to 5, typically from 0.2 to 5, and in particular from 0.25 to 5, and more particularly from 0.5 to 2 or from 0.2 to 1.2, even from 0.4 to 1.2

More particularly, the extraction process of unsaponifiable fraction is such that liquid/liquid extraction is performed by putting the DHS in contact a first solvent system, especially in a counter-current process, by means of a first solvent system such as defined hereinabove and comprising, or even consisting in, MIBK, and optionally HMDS, advantageously the ratio (volume/volume) of solvent system/DHS ranging from 0.1 to 10, especially from 0.25 to 5, in particular from 0.5 to 2.

More particularly, the extraction process of unsaponifiable fraction is such that liquid/liquid extraction is carried out by putting DHS in contact with a first solvent system, especially in a counter-current process, by means of a first solvent system such as defined hereinabove and comprising, or even consisting in, of DIPE, and optionally HMDS, advantageously the ratio (volume/volume) of solvent system/DHS ranging from 0.1 to 10, especially from 0.25 to 5, in particular from 0.5 to 2.

More particularly, the extraction process of unsaponifiable fraction is such that liquid/liquid extraction is carried out by putting DHS in contact with a first solvent system, especially in a counter-current process, by means of a first solvent system such as defined hereinabove and comprising, or even consisting in, ethyl propionate, and optionally HMDS, advantageously the ratio (volume/volume) of solvent system/DHS ranging from 0.1 to 10, especially from 0.25 to 5, in particular from 0.5 to 2.

More particularly, the type of continuous phase can be either the DHS to be extracted, or the extraction solvent. The type of continuous phase is defined as a function of the alcoholic titre of the prepared DHS, of the ratio between the volumes or flow rates of contacted DHS and solvent, and of the unsaponifiable under consideration.

The vegetable oil or the oil originating from micro-organism used in the present process can be selected from soy oil, quinoa, rapeseed, maize, sunflower, sesame, lupin, cotton, coconut, olive, palm, wheat germ, lucern, avocado, palm nut, peanut, copra, flax, castor, grape pips, squash seeds, blackcurrant seeds, melon seeds, tomato seeds, pumpkin seeds, almond, hazelnut, walnut, evening primrose, borage, safflower, camelina, poppy, macro-algae, micro-algae, such as *Chorella*, and/or originate from micro-organisms, especially marine, fresh water or land water, in particular yeasts, mold, and more particularly, bacteria, and their mixtures.

The vegetable butter can be selected from cocoa butter, illipe butter, shea butter, and their mixtures.

The comparison of unsaponifiable contents from different vegetable oils: soy, cotton, coconut, olive and avocado, shows that avocado oil obtained by extraction following various known processes, comprises a particularly large rate of unsaponifiable.

Typically, the contents of unsaponifiable fraction obtained range from 2 to 10% in avocado oil, are of around 0.5% in coco oil, around 1% in soy oil and around 1% in olive oil.

The unsaponifiable of avocado can be prepared by extraction from avocado oil.

The extraction process of unsaponifiable from avocado oil can be performed as follows.

According to a method known to the person skilled in the art, to extract the oil:
- either the fresh pulp is pressed in the presence of an outside fibrous body which absorbs water, such as parchment coffee, in a cage press, then the emulsion of oil and water obtained by decantation and/or centrifugation is separated;
- or the fresh pulp is ground and put in contact with an adapted organic solvent (for example a methanol-chloroform mixture) then the oil is recovered by evaporation of the solvent.

Several processes have been described in the prior art for extracting unsaponifiable fraction from vegetable oil.

A particular example is the preparation process of an unsaponifiable of avocado oil such as described and claimed in patent FR 2,678,632.

So, unsaponifiable of avocado oil used according to the invention can be obtained from fresh fruit, but preferably unsaponifiable of avocado is prepared from fruit previously treated thermally, prior to extraction of the oil and saponification, as described in patent FR 2,678,632.

This thermal treatment consists of controlled drying of the fruit, preferably fresh fruit, over at least four hours, advantageously at least 10 hours, preferably between around 24 and around 48 hours, at a temperature preferably of at least around 80° C. and preferably between around 80 and around 120° C.

Another example is the process for preparation of unsaponifiable of soy oil, obtained from a concentrate of unsaponifiable of soy oil.

Said unsaponifiable concentrate is prepared by molecular distillation according to a process such as described for lupin oil in patent application FR 2,762,512, but adapted to soy oil.

In this process, soy oil is distilled in a molecular distiller of centrifuge or scrap film type, at a temperature comprised between around 210 and 250° C. and under high vacuum, of between 0.01 and 0.001 millimeters of mercury (or 0.13 to 1.3 Pa).

The distillate obtained has a content of unsaponifiable between 5 and 40% in volume and therefore constitutes a concentrate of unsaponifiable of soy oil.

The concentrate is then saponified by a base such as potash or the soda in polar medium, especially alcoholic, preferably ethanol, n-propanol, iso-propanol, butanol, in particular n-butanol, MeTHF, or a mixture thereof, and it then undergoes one or more extractions by the first solvent system.

The extraction solution obtained is preferably then centrifuged, filtered then washed in water to eliminate residual traces of alkalinity.

The extraction solvent is carefully evaporated to recover unsaponifiable.

Finally, prior to its saponification, the oil can be previously enriched in unsaponifiable by separating a majority of the constituents of the unsaponifiable, which are recovered in a concentrate. Different methods can be used: cold crystallisation, liquid/liquid extraction, or molecular distillation.

Prior concentration of unsaponifiable oil decreases the volumes of oil to be saponified.

Molecular distillation is particularly preferred, being carried out preferably at a temperature comprised between around 180 and around 230° C. by maintaining a pressure comprised between $10^{-3}$ and $10^{-2}$ mm Hg and preferably of the order of $10^{-3}$ mm Hg.

The concentration in unsaponifiable of the distillate can reach 60% in mass relative to the total mass.

Quite particularly, the present invention relates to a process such as described hereinabove in which unsaponifiable obtained is selected from an unsaponifiable of soy, an unsaponifiable of avocado, especially an unsaponifiable of avocado rich in furanic fraction and/or an unsaponifiable of avocado rich in sterolic fraction.

The process according to the present invention allows for extraction of an unsaponifiable fraction contained in vegetable oil, an oil originating from a micro-organism or a vegetable butter, and it can also allow for the extraction of an unsaponifiable fraction from a co-product of the refining industry for vegetable oils or oils originating from a micro-organism, such as for example deodorisation exhaust, also called deodistillates, produced within the refining of vegetable oils or oils originating from micro-organisms.

Fatty acids and partial glycerides present in the deodistillates can indeed be saponified or esterified by light alcohol, the aim of which is to separate the fatty fraction from unsaponifiable fraction, either by liquid/liquid extraction or by vacuum distillation.

Finally, purification of unsaponifiable or active separated fractions, most often tocopherols (including vitamin E) and sterols, especially uses crystallisation steps in an organic solvent or liquid/liquid extraction.

Another object of the present invention is an extraction process of an unsaponifiable fraction in a co-product of the refining industry from a vegetable oil or an oil originating from a micro-organism, such that this co-product is a deodistillate of a vegetable oil or an oil originating from a micro-organism, said process comprising at least:
 a saponification step transforming the deodistillate into a hydro-alcoholic solution,
 a counter-current extraction step of the hydro-alcoholic solution by means of the first solvent system,
 a crystallisation step of sterols and/or triterpenic alcohols,
 a separation step of an active compound, such as tocopherols, tocotrienols, squalene and carotenes, said separation step being selected in the group formed by extractions, in particular by means of the first solvent system, and distillations.

Quite particularly, the crystallisation of sterols and/or triterpenic alcohols can be performed in the first solvent system.

Yet another object of the present invention is an unsaponifiable fraction, especially partial or total, devoid of solvents classified in the list CMR UE1, UE2 and/or US, able to be obtained by the extraction process according to the present invention; in particular said fraction is directly obtained by the extraction process according to the present invention.

The present invention further relates to the use of this fraction for the preparation of a composition, especially pharmaceutical, alimentary and/or cosmetic, or of a food complement.

Another object of the present invention is an unsaponifiable fraction, especially partial or total, devoid of solvents classified in the list CMR UE1, UE2 and/or US, such as described hereinabove, for its use as a medicament, as medical device, as dermatological agent, as cosmetic agent, or as nutraceutical, for human or animal use, advantageously in the prevention and/or the treatment of conditions in connective tissue such as arthrosis, articular pathologies such as rhumatisms, parodontal diseases such as the gingivitis or the parodontitis, or even in the prevention and/or treatment of conditions of the dermis and/or of the hypodermis such as cutaneous ageing, stretch marks and cellulite, or conditions of the epidermal barrier such as cutaneous inflammations, atopical eczema and irritative and/or inflammatory dermatitis.

Yet another object of the present invention is a composition, especially alimentary, cosmetic or pharmaceutical, or an alimentary complement, comprising at least one unsaponifiable fraction of at least one vegetable oil or of an oil originating from a micro-organism, said fraction being devoid of solvents classified in the list CMR UE1, UE2 and/or US and/or said fraction being susceptible to be obtained, or obtained directly, by the process according to the invention, and said composition optionally comprising an excipient, in particular cosmetically, alimentarily or pharmaceutically acceptable.

According to a particular embodiment, the present invention relates to a composition, especially pharmaceutical, alimentary or cosmetic, or an alimentary complement, comprising at least one unsaponifiable, in particular an unsaponifiable of soy, an unsaponifiable of avocado, quite particularly an unsaponifiable of avocado rich in furanic fraction and/or an unsaponifiable of avocado rich in sterolic fraction, susceptible to be obtained or directly obtained by the process according to the invention.

The compositions according to the invention can be intended for the prevention and/or treatment of conditions of connective tissue, especially arthrosis, parodonthopathies, cutaneous ageing and/or cutaneous inflammations.

The compositions cosmetic according to the invention can be intended for the prevention and/or treatment of cutaneous conditions of the epidermis of the dermis and/or of the hypodermis.

In the sense of the present invention <<devoid of solvents classified in the list<<CMR UE1, UE2 and/or US>> means a total content of solvents classified in the list CMR UE1, UE2 and/or US inferior to 10 ppm, especially inferior to 5 ppm, in particular inferior to 2 ppm, or even inferior to 1 ppm.

Another object of the present invention is a process for cosmetic treatment such as the composition cosmetic according to the invention being applied topically.

The invention also relates to an unsaponifiable from a vegetable oil, from an oil originating from a micro-organism or a vegetable butter obtained or susceptible to be obtained by the process according to the present invention for its use as a medicament, in particular intended for treating or preventing conditions of the connective tissue, especially arthrosis.

According to yet another aspect, an object of the invention is the use of HMDS, in a content ranging from 0.1 to 49%, typically from 0.1 to 45%, in volume, relative to the total volume of extraction solvents, in a liquid/liquid extraction process of unsaponifiable, advantageously from a hydro-alcoholic solution.

In particular, HMDS is present in a content ranging from 0.5 to 25%, or even from 1 to 10%, and quite particularly from 5 to 10% in volume, relative to the total volume of solvent.

In particular, said process according to the invention comprises a solvent system comprising:
- at least one solvent comprising at least 5 carbon atoms, or even from 5 to 8 carbon atoms, and one or two oxygen atoms in the form of ether, ketone or ester function, in particular at least one solvent selected from
  - methylketones, especially MIBK, 2-heptanone,
  - propionates, especially ethyl propionate, n-butyl propionate, isoamyl propionate,
  - propylethers, especially DIPE, and
  - a mixture of the latter, or
- at least one solvent selected from
  - aromatic fluorinated solvents, especially trifluorotoluene (BTF) and hexafluorobenzene (BHF),
  - tert-butyl ethers, especially 2-ethoxy-2-methylpropane, again called ethyl-tert-butyl-ether (ETBE),
  - solvents comprising at least one silicon atom, especially hexamethyldisiloxane (HMDS) and tetramethylsilane (TMS),
  - methyl-tetrahydrofurane (MeTHF), and
  - their mixtures, or
- a mixture of solvents as hereinabove.

The content of these solvents can be such as described hereinabove.

The CAS numbers of these different solvents are the following BTF: 98-08-8; BHF: 392-56-3; ETBE: 637-92-3; TMS: 75-76-3; and MeTHF: 96-47-9.

HMDS can especially modulate the extractive capacity of the solvent system. So, the presence of HMDS among extraction solvents can refine the profile of the unsaponifiable obtained, improve the overall extraction yield and/or the extraction rate in one or more fractions.

Also, the presence of HMDS in content such as defined hereinabove in a solvent system can diminish the consumption of solvents, washing water and/or extraction time. This can make decantation easier and cause less formation of emulsions and/or faster dephasing during the extraction and/or washing steps.

HMDS can be used as an agent for improvement of the yield and/or of the extraction rate, as modulating agent of unsaponifiable profiles, dephasing agent and/or acceleration agent.

Of course, the different characteristics disclosed in the present description can be combined together.

By way of examples illustrating the present invention, the following experiments have been conducted.

EXAMPLES

Example 1: Extraction of Unsaponifiable of Avocado with DCE (Reference 1)

The first step consists of saponifying a concentrate prepared by molecular distillation of avocado oil.

For this purpose, a given mass of fatty matter of avocado (15.6 g) then ethanol (36.6 mL), potash at 50% (5.2 mL) and a few grains of pumice stone are successively introduced in a balloon of 100 ml provided with a refrigerant.

The system is then brought to reflux for 3 h30 then, after cooling, diluted with demineralised water which modifies the titre of alcohol of the solution saponified at 21% mass.

The resulting diluted hydro-alcoholic solution contains unsaponifiable (or fraction of unsaponifiable) in solution. This unsaponifiable is then extracted by a first solvent system, in this case DCE.

Several successive extractions (5×60 mL) are carried out; the organic phases collected in this way are then combined and washed in water (5×150 mL) to neutrality.

The resulting solvent phase is dried on anhydrous sodium sulfate then filtered; unsaponifiable is then recovered by evaporation of the solvent in the rotary evaporator at a temperature of 60° C. and pressure of the order of 300 mbar; it is then dried under high vacuum.

The extracted unsaponifiable is weighed and stored in a pill dispenser in inert atmosphere. The results are presented in Table 1 hereinbelow.

Example 2: Extraction of Unsaponifiable of Avocado with 2-Heptanone

Extraction is performed according to the operating method of Example 1 which, after optimisation to adapt it to the new solvent system, corresponds to:
- a dilution step for adjusting the titre of alcohol to 21% mass;
- an extraction step with 5×60 ml of 2-heptanone;
- a washing step of the organic phases with 6×150 mL of water.

The measurements are taken as in Example 1 and the results are presented in Table 1 hereinbelow.

Example 3: Extraction of Unsaponifiable of Avocado with Isoamyl Propionate

Extraction is performed according to the operating method of Example 1 which, after optimisation to adapt it to the new solvent system, corresponds to:
- a dilution step for adjusting the titre of alcohol to 22% mass;
- an extraction step with 5×60 ml isoamyl propionate;
- a washing step of the organic phases with 6×150 mL of water.

The measurements are taken as in Example 1 and the results are presented in Table 1 hereinbelow.

Example 4: Extraction of Unsaponifiable of Avocado with n-Butyl Propionate

Extraction is performed according to the operating method of Example 1 except that the quantities of materials used are divided by 2.

After optimisation to adapt it to the new solvent system, the operating method used corresponds to:
- a dilution step for adjusting the titre of alcohol to 22% mass;
- an extraction step with 5×30 mL of isoamyl propionate;
- a washing step of the organic phases with 6×75 mL of water.

The measurements are taken as in Example 1 and the results are presented in Table 1 hereinbelow.

TABLE 1

Delta of yield between the reference process (extraction on DCE - Example 1) and the processes described in Examples 2 to 4

|  | Unsaponifiable mass yield (%) | Yield gain (%) |
|---|---|---|
| Example 1 | 38.7 | 0 |
| Example 2 | 47.6 | +23 |
| Example 3 | 48.4 | +25 |
| Example 4 | 51.7 | +34 |

The unsaponifiable mass yield is calculated as follows:

R=100×(mass of extracted unsaponifiable/mass of concentrate used)

The yield gain is calculated as follows:

G=100×[(R linked to the solvent S−R linked to the reference solvent)/R linked to the reference solvent]

The results show that unsaponifiable mass yield of the processes according to the invention is improved relative to the process involving DCE.

Example 5: Extraction of Unsaponifiable of Soy with DCE (Reference 2)

The first step consists of saponifying a deodistillate of soy. For this purpose, a given mass of deodistillate of soy (10 g) then ethanol (23.3 mL), potash at 50% (1.7 mL) and a few grains of pumice stone are successively introduced to a balloon of 100 ml provided with a refrigerant.

The system is then brought to reflux for 3 h00 then, after cooling, diluted with demineralised water, which modifies the titre of alcohol of the solution saponified at 23% mass.

The hydro-alcoholic solution diluted obtained contains unsaponifiable (or fraction of unsaponifiable) in solution. This unsaponifiable is then extracted by a first solvent system, in this case DCE.

Several successive extractions (5×36 mL) are carried out; the collected organic phases are then combined and washed in city-supply water (5×90 mL) to neutrality.

The resulting solvent phase is dried on anhydrous sodium sulfate then filtered; unsaponifiable is then recovered by evaporation of the solvent in the rotary evaporator at a temperature of 60° C. and pressure of the order of 300 mbar; it is then dried under high vacuum.

The extracted unsaponifiable is weighed and stored in a pill dispenser in inert atmosphere. The results are presented in Table 2 hereinbelow.

Example 6: Extraction of Unsaponifiable of Soy with MIBK

Extraction is performed according to the operating method of Example 6 which, after optimisation to adapt it to the new solvent system, corresponds to:
a dilution step for adjusting the titre of alcohol to 23% mass;
an extraction step with 2×105 mL of MIBK;
a washing step of the organic phases with 6×105 mL of water.

The measurements are taken as in Example 5 and the results are presented in Table 2 hereinbelow.

Example 7: Extraction of Unsaponifiable of Soy with Ethyl Propionate

Extraction is performed according to the operating method of Example 6 which, after optimisation to adapt it to the new solvent system, corresponds to:
a dilution step for adjusting the titre of alcohol to 23% mass;
an extraction step with 5×60 mL of ethyl proprionate;
a washing step of the organic phases with 6×150 mL of water.

The measurements are taken as in Example 5 and the results are presented in Table 2 hereinbelow.

Example 8: Extraction of Unsaponifiable of Soy with a Mixture of MIBK and HMDS 90/10 v/v Extraction is performed according to the operating method of Example 5 which, after optimisation to adapt it to the new solvent system, corresponds to:
a dilution step for adjusting the titre of alcohol to 24% mass;
an extraction step with 2×105 mL of a mixture MIBK/HMDS 90/10 v/v;
a washing step of the organic phases with 6×105 mL of water.

The measurements are taken as in Example 5 and the results are presented in Table 2 hereinbelow.

TABLE 2

Delta of yield between the reference process (extraction on DCE - Example 5) and the processes described in Examples 6 to 8

|  | Unsaponifiable mass yield (%) | Yield gain (%) |
|---|---|---|
| Example 5 | 46.2 | 0 |
| Example 6 | 50.4 | +9 |
| Example 7 | 50.0 | +8 |
| Example 8 | 45.0 | −3 |

The unsaponifiable mass yield, is calculated as follows:

R=100×(mass of extracted unsaponifiable/mass of concentrate used)

The gain in yield is calculated as follows:

G=100×[(R linked to the solvent S−R linked to the reference solvent)/R linked to the reference solvent]

Examples 6 and 7 show that unsaponifiable mass yield of the processes according to the invention is improved relative to the process involving DCE.

By remaining within a range of unsaponifiable mass yield close to the target Example 8 also gains in dephasing quality and therefore in overall extraction time.

Example 9: Extraction of Unsaponifiable from Avocado Counter-Current with DCE The assay described in Example 1 was transposed to pilot scale by conducting counter-current extraction in an agitated column. The titre of the hydro-alcoholic solution was adjusted to 24% after saponification via a dilution step. On start-up of extraction the column was filled with solvent (continuous phase) and the ratio between the flow rates of the solvent or organic phase and DHS or diluted hydro-alcoholic solution was fixed at 1.2.

The weight yield of this extraction was calculated and was 42%.

Example 10: Extraction of Unsaponifiable from Soy Counter-Current with DCE

The assay described in Example 5 was transposed to pilot scale by conducting counter-current extraction in an agitated column. The titre of the hydro-alcoholic solution was adjusted to 23% after saponification via a dilution step. On start-up of extraction the column was filled with solvent (continuous phase) and the ratio between the flow rates of the solvent or organic phase and DHS or diluted hydro-alcoholic solution was fixed at 1.2.

The weight yield of this extraction was calculated and was 40%.

Example 11: Extraction of Unsaponifiable from Avocado Counter-Current with MIBK The assay described in Example 6 was transposed to pilot scale on avocado matrix by conducting counter-current extraction in an agitated column. The titre of the hydro-alcoholic solution was adjusted to 14% after saponification via a dilution step. On start-up of extraction the column was filled with solvent (continuous phase) and the ratio between the flow rates of the solvent or organic phase and DHS or diluted hydro-alcoholic solution was fixed at 0.9.

The weight yield of this extraction was calculated and was 50%.

Example 12: Extraction of Unsaponifiable from Avocado Counter-Current with MIBK The assay described in Example 6 was transposed to pilot scale on avocado matrix by conducting counter-current extraction in an agitated column. The titre of the hydro-alcoholic solution was adjusted to 14% after saponification via a dilution step. On start-up of extraction the column was filled with hydro-alcoholic solution (continuous phase) and the ratio between the flow rates of the solvent or organic phase and DHS or diluted hydro-alcoholic solution was set at 0.38.

The weight yield of this extraction was calculated and was 45%.

Example 13: Extraction of Unsaponifiables from Soy Counter-Current with MIBK The assay described in Example 6 was transposed to pilot scale by conducting counter-current extraction in an agitated column. The titre of the hydro-alcoholic solution was adjusted to 24% after saponification via a dilution step. On start-up of extraction the column was filled with solvent (continuous phase) and the ratio between the flow rates of the solvent or organic phase and DHS or diluted hydro-alcoholic solution was fixed at 1.2.

The weight yield of this extraction was calculated and was 39%.

The table below summarises the results obtained:

| Solvent | Soy | | Avocado | | |
| --- | --- | --- | --- | --- | --- |
| | DCE | MIBK | DCE | MIBK | MIBK |
| Example N° | 10 | 13 | 9 | 11 | 12 |
| Continuous phase | Solvent | Solvent | Solvent | Solvent | Aqueous |
| Alcohol titre | 23% | 24% | 24% | 14% | 14% |
| Flow rate ratio | 1.2 | 1.2 | 1.2 | 0.90 | 0.38 |
| Yield | 40% | 39% | 42% | 50% | 45% |

The assays carried out show that the choice of DHS alcohol titre has an influence on phase partitioning and allows the extraction yield to be optimised.

The invention claimed is:

1. A process for extraction of an unsaponifiable fraction contained in an oil or a vegetable butter, in an oil originating from a micro-organism, in a concentrate of oil or vegetable butter or of oil originating from a micro-organism, or in a co-product of the refining industry for vegetable oils or oils originating from micro-organisms, comprising at least the following steps:
   A) saponifying said oils, said butter or said co-product of the refining industry for vegetable oils or oils originating from micro-organisms to form a hydro-alcoholic solution,
   A') adjusting alcohol content of the hydro-alcoholic solution obtained in step A to between 10 and 50% by weight, and
   B) extracting the adjusted hydro-alcoholic solution, wherein the fatty fraction is separated from unsaponifiable fraction by liquid/liquid extraction,
   wherein at least the liquid/liquid extraction step of the step B is performed with a first solvent system comprising a content in solvent selected from the solvents comprising at least 5 carbon atoms and one or two oxygen atoms in the form of either ether function, or ketone function, or ester function, of at least 50% in volume relative to the total volume of the first solvent system,
   wherein said solvent comprising at least 5 carbon atoms and one or two oxygen atoms is selected from methylketones, propionates, propylethers, and mixtures thereof.

2. The process according to claim 1, wherein after step A' the alcohol content is between 11 and 40% by weight.

3. The process according to claim 1, further comprising after step B a purification step C of the unsaponifiable.

4. The process according to claim 3, wherein purification step C of the unsaponifiable is performed with said first solvent system.

5. The process according to claim 1, wherein the first solvent system has a density less than 1.

6. The process according to claim 1, wherein the solvent comprising at least 5 carbon atoms and one or two oxygen atoms is selected from methyl isobutyl ketone (MIBK), 2-heptanone, ethyl propionate, n-butyl propionate, isoamyl propionate, diisopropyl ether (DIPE), and mixtures thereof.

7. The process according to claim 1, wherein the first solvent system comprises a content in solvent comprising at least 5 carbon atoms and one or two oxygen atoms in the form of ether, ketone or ester function of at least 75% in volume, relative to the total volume of the first solvent system.

8. The process according to claim 1, wherein the first solvent system comprises a content in solvent selected from solvents comprising at least 5 carbon atoms and one or two oxygen atoms in the form of ether, ketone or ester function, selected from methylketones, propionates, propylethers, and mixtures thereof of at least 75% in volume, relative to the total volume of the first solvent system.

9. The process according to claim 1, wherein the first solvent system further comprises hexamethyldisiloxane (HMDS) in a content ranging from 0.1 to 49% in volume relative to the total volume of the first solvent system.

10. The process according to claim 1, wherein the first solvent system comprises a content of Carcinogenic, Mutagenic and Toxic for Reproduction (CMR) solvent(s), present on the list CMR UE1, UE2, and/or US, less than or equal to 0.1% in volume, relative to the total volume of the first solvent system.

11. The process according to claim 1, wherein step A) is performed in a second solvent system comprising a content in solvent selected from C2 to C4 alcohols, 2-methyltetrahydrofuran (MeTHF) and their mixtures, of at least 50% in volume relative to the total volume of the second solvent system.

12. The process according to claim 11, wherein the second solvent system comprises a content in solvent selected from C2 to C4 alcohols, 2-methyltetrahydrofuran (MeTHF) and their mixtures, of at least 60% in volume, relative to the total volume of the second solvent system.

13. The process according to claim 11, wherein the second solvent system comprises a content of CMR solvent(s) present on the list CMR UE1, UE2 and/or US, less than or equal to 0.1% in volume, relative to the total volume of the second solvent system.

14. The process according to claim 1, wherein the titre of alcohol of the hydro-alcoholic solution is comprised between 10 and 50% in mass.

15. The process according to claim 1, wherein:
the vegetable oil or the oil originating from micro-organism used in the present process is selected from soy oil, quinoa, rapeseed, maize, sunflower, sesame, lupin, cotton, coconut, olive, palm, wheat germ, lucern, avocado, palm nut, peanut, copra, flax, castor, grape pips, squash seeds, blackcurrant seeds, melon seeds, tomato seeds, pumpkin seeds, almond, hazelnut, walnut, evening primrose, borage, safflower, camelina, poppy, macro-algae, micro-algae, and/or originate from micro-organisms, and their mixtures, and
the vegetable butter is selected from cocoa butter, illipe butter, shea butter, and their mixtures.

16. The process according to claim 1, wherein the unsaponifiable obtained is selected from an unsaponifiable of soy, an unsaponifiable of avocado, an unsaponifiable of avocado rich in furanic fraction or an unsaponifiable of avocado rich in sterolic fraction.

17. The process according to claim 2, wherein after step A' the alcohol content is between 12 and 28% by weight.

18. The process according to claim 1, wherein the first solvent system comprises a content in solvent comprising at least 5 carbon atoms and one or two oxygen atoms in the form of ether, ketone or ester function of at least 90% in volume, relative to the total volume of the first solvent system.

19. The process according to claim 1, wherein the first solvent system comprises a content of methylketones or propionates of at least 90% in volume, relative to the total volume of the first solvent system.

20. The process according to claim 8, wherein the solvent comprising at least 5 carbon atoms and one or two oxygen atoms is selected from methyl isobutyl ketone (MIBK), 2-heptanone, ethyl propionate, n-butyl propionate, isoamyl propionate, diisopropyl ether (DIPE), and mixtures thereof.

21. The process according to claim 11, wherein the C2 to C4 alcohols are ethanol, n-propanol, iso-propanol and/or butanol.

22. The process according to claim 12, wherein the C2 to C4 alcohols are ethanol, n-propanol, iso-propanol and/or butanol.

23. The process according to claim 15, wherein said micro-algae is *Chorella*.

* * * * *